United States Patent
Nono et al.

(10) Patent No.: US 10,822,372 B2
(45) Date of Patent: Nov. 3, 2020

(54) USE OF PARTICULAR COMBINATIONS OF CARBOHYDRATES FOR STABILIZING PROTEINS, AND PROTEIN COMPOSITIONS CONTAINING SUCH COMBINATIONS

(71) Applicant: Roquette Freres, Lestrem (FR)

(72) Inventors: Merveille Nono, Bethune (FR); Nicolas Descamps, Sainghin-En-Melantois (FR); Denis Simon, Leffrinckoucke (FR); Olaf Haeusler, Fletre (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 15/563,871

(22) PCT Filed: Mar. 30, 2016

(86) PCT No.: PCT/FR2016/050709
§ 371 (c)(1),
(2) Date: Oct. 2, 2017

(87) PCT Pub. No.: WO2016/156734
PCT Pub. Date: Oct. 6, 2016

(65) Prior Publication Data
US 2018/0118779 A1    May 3, 2018

(30) Foreign Application Priority Data

Apr. 3, 2015  (FR) .................... 15 52899

(51) Int. Cl.
*C07K 1/113* (2006.01)
*C12N 9/24* (2006.01)

(52) U.S. Cl.
CPC .......... *C07K 1/1136* (2013.01); *C12N 9/2402* (2013.01); *C12Y 302/01002* (2013.01)

(58) Field of Classification Search
None
See application file for complete search history.

(56) References Cited

U.S. PATENT DOCUMENTS

| | | |
|---|---|---|
| 4,891,319 A | 1/1990 | Roser |
| 7,838,055 B2 | 11/2010 | Eroma et al. |
| 2013/0224248 A1* | 8/2013 | Taylor ................ A61K 9/0019 424/239.1 |

FOREIGN PATENT DOCUMENTS

| | | | |
|---|---|---|---|
| EP | 0 750 843 A2 | 1/1997 | |
| RU | 2 470 520 C1 | 12/2012 | |
| WO | WO 91/18091 A1 | 11/1991 | |
| WO | WO 98/00530 A1 | 1/1998 | |
| WO | WO-2015021600 A1 * | 2/2015 | ........... C12N 9/2425 |

OTHER PUBLICATIONS

X. Liu et al., "Effects of Polyols on the Stability of Whey Proteins in Intermediate-Moisture Food Model Systems." Journal of Agricultural and Food Chemistry, vol. 57, pp. 2339-2345, 2009.
L. Nicoud et al., "Effect of Polyol Sugars on the Stabilization of Monoclonal Antibodies." Biophysical Chemistry, vol. 197, pp. 40-46, 2015.
K. Gekko et al., "Amino Acid Solubility and Protein Stability in Aqueous Maltitol Solutions." Agric. Biol. Chem., vol. 53, No. 1, pp. 89-95, 1989.
S. Kadoya et al., "Freeze-Drying of Proteins with Glass-Forming Oligosaccharide-Derived Sugar Alcohols." International Journal of Pharmaceutics, vol. 389, pp. 107-113, 2010.
M.T. Cicerone et al., "Substantially Improved Stability of Biological Agents in Dried Form." BioProcess International, pp. 36-47, Jan. 2003.

* cited by examiner

*Primary Examiner* — Marsha Tsay
(74) *Attorney, Agent, or Firm* — Oliff PLC

(57) ABSTRACT

One subject of the present invention is the use of a combination of a polyol (i) consisting of 12 carbon atoms and of a polyol (ii) consisting of 4 to 6 carbon atoms, as protein stabilizer. Another subject of the present invention is protein compositions comprising such a combination. A final subject of the present invention is a process for preparing protein compositions using such a combination.

5 Claims, No Drawings

USE OF PARTICULAR COMBINATIONS OF CARBOHYDRATES FOR STABILIZING PROTEINS, AND PROTEIN COMPOSITIONS CONTAINING SUCH COMBINATIONS

This application is a national stage of International Application No. PCT/FR2016/050709 filed on Mar. 30, 2016, which claims the benefit of FR 15 52899 filed Apr. 3 2015, the contents of each of which are incorporated herein by reference.

A subject of the present invention is the use of a combination of a polyol (i) consisting of 12 carbon atoms and of a polyol (ii) consisting of 4 to 6 carbon atoms, as protein stabilizer. A subject of the present invention is also protein compositions comprising such a combination. Finally, a subject of the present invention is a process for preparing protein compositions using such a combination.

PRIOR ART

The past few decades have seen an acceleration in the development of therapeutic products derived from biotechnologies, and in particular biomedicaments, which are today mainly represented by therapeutic proteins.

Only the intrinsic characteristics of proteins are responsible for a specific galenic problem for developing these medicaments. Their high molecular weight combined with their low resorption—and thus with low bioavailability—and also their sensitivity to digestive proteases considerably limit the possible modes for their administration, and in particular do not make it possible to use the oral route. It is for this reason that the injectable routes are currently preferred.

Proteins are also characterized by their instability, their sensitivity to variations in the surrounding conditions, such as the temperature or the pH, and by a potential interaction with the hydrophobic surfaces of their container. These parameters must be strictly controlled because denaturation of the proteins and structural modification thereof can cause, in the patient, not only an impairment of their therapeutic efficacy, but also harmful immune reactions.

Unfortunately, the industrial production of proteins involves processes which can easily denature the latter. One of the main challenges lies in their ability to resist these industrial treatments. Such treatments are typically cryogenization, lyophilization, or else heat treatments used for purification or viral inactivation purposes, at temperatures close to that of the denaturation of the proteins.

It must also be possible to preserve the protein conformation during storage of the proteins. This is all the more true since, in the injectable protein field, the industry is increasingly seeking to replace lyophilized products with products already in solution.

In order to overcome these stability problems, the prior art mentions the use of various agents, for example trehalose, amino acids such as arginine and lysine, carrier proteins, hydrocolloids, surfactants, native or modified cyclodextrins, and solvents.

Trehalose is the main carbohydrate used for this application, and has been the subject of various patent applications (for example the application granted under number US 4 891 319 A). This sugar is a disaccharide consisting of 12 carbon atoms, which is in practice generally used in combination with carrier proteins and/or hydrocolloids.

The main problem with trehalose is that it is a rare sugar, the synthesis of which is particularly complex and expensive. It is thus difficult to produce large amounts thereof. Furthermore, it has a glycemic index such that it is not recommended for diabetic patients.

It is to the applicant's credit to have succeeded in developing a stabilizer additive consisting of carbohydrates, that is particularly useful for protein stabilization. This additive, which is much easier to access than trehalose, consists of a combination of a first polyol (i) consisting of 12 carbon atoms, preferentially maltitol, and of a second polyol (ii) consisting of 4 to 6 carbon atoms, preferentially sorbitol, xylitol and/or mannitol.

The use, for stabilizing proteins, of polyols effectively consisting of 12 carbon atoms has already been described in the prior art. Likewise, the use of polyols effectively consisting of 4 to 6 carbon atoms has already been described. However, it has never been envisioned to combine them. More generally, the prior art is extremely poor in terms of carbohydrate mixtures. It is nevertheless possible to mention in this regard:

the article Cicerone M T; Tellington A; Trost I; Sokolov A. Substantially improved stability of biological agents in dried form: The role of glassy dynamics in preservation of biopharmaceuticals. BioProc. Int. 1: 36-47 (2003).

patent application WO 98/00530, which describes an additive composed of a disaccharide, of a disaccharide derivative, of a carrier protein and of a polysaccharide.

These publications do not disclose the use of a combination of a polyol consisting of 12 carbon atoms with a polyol consisting of 4 to 6 carbon atoms.

It is interesting to add that the use of maltitol, which is the preferred C12 polyol in the present invention, is only rarely exemplified in the prior art. Moreover, the published experimental data do not reveal a particular effectiveness of the latter. Some data go as far as pointing out the lack of performance of maltitol.

AIMS OF THE INVENTION

A first objective of the invention consists of the provision of a stabilizing agent which has equivalent or improved properties compared with trehalose.

An objective of the invention is in particular to respond to the abovementioned problem by providing a protein-stabilizing agent which is easier to access than trehalose.

An objective of the invention is in particular to respond to the abovementioned problems by providing a biobased stabilizing agent, derived from carbohydrate technology.

SUMMARY OF THE INVENTION

A first subject of the present invention is the use of a combination of a polyol (i) consisting of 12 carbon atoms and of a polyol (ii) consisting of 4 to 6 carbon atoms, as protein stabilizer.

A second subject of the present invention is a protein composition comprising a protein, a polyol (i) consisting of 12 carbon atoms and a polyol (ii) consisting of 4 to 6 carbon atoms.

A third subject of the present invention is a process for preparing such a composition, comprising mixing a protein with a polyol (i) consisting of 12 carbon atoms and a polyol (ii) consisting of 4 to 6 carbon atoms.

DETAILED DESCRIPTION OF THE INVENTION

The applicant has shown that there is a synergy between the polyol (i) consisting of 12 carbon atoms, in particular maltitol, and the polyol (ii) consisting of 4 to 6 carbon atoms.

This synergy does not occur when a combination not in accordance with the invention is used, i.e. when a sugar is used instead of a polyol and/or when the polyols do not have the appropriate number of carbon atoms.

Furthermore, the results obtained in absolute values are better when a combination in accordance with the invention is used, compared with trehalose alone, or compared with other combinations of carbohydrates not in accordance with the invention.

This emerges in particular from the results of the tests presented in example 1 below.

The combination in accordance with the invention can be obtained from biobased compounds, derived from carbohydrate technology, that are easy to access and to process.

The combination in accordance with the invention has, moreover, the advantage of a good fit between the amount that can be solubilized and the viscosity of the resulting solution. This is particularly advantageous in the field of injectable solutions.

The protein compositions comprising the combination according to the invention also have the advantage of good chemical stability, owing to the low reactivity of the compounds used in this combination.

In the combination according to the invention, the polyol (i) consisting of 12 carbon atoms can be a single compound, preferentially maltitol, or a mixture of polyols consisting of 12 carbon atoms. Likewise, the polyol (ii) consisting of 4 to 6 carbon atoms can be a single compound, or a mixture of polyols consisting of 4 to 6 carbon atoms.

It is thus understood, in the present invention, that when reference is made to a composition comprising the combination in accordance with the invention, the polyol (i) includes all the polyols consisting of 12 carbon atoms of the composition, and the polyol (ii) includes all the polyols consisting of 4 to 6 carbon atoms of the composition.

In the combination according to the invention, the polyol (i) consisting of 12 carbon atoms preferentially comprises maltitol, in a content preferentially greater than 50%, preferentially greater than 70%, most preferentially greater than 90%, these percentages being expressed by dry weight of maltitol relative to the total dry weight of the polyols consisting of 12 carbon atoms. Preferentially, the polyol (i) is solely composed of maltitol.

In the combination according to the invention, the polyol (ii) consisting of 4 to 6 carbon atoms preferentially consists of 5 or 6 carbon atoms, and is preferentially chosen from sorbitol, mannitol, xylitol, or a mixture thereof. It preferentially consists of 6 carbon atoms, and is preferentially chosen from sorbitol, mannitol, or a mixture thereof, for example a mixture in a dry weight ratio equal to 50/50.

Preferentially, the dry weight ratio between the polyol (i) and the polyol (ii) of the composition according to the invention ranges from 5/95 to 95/5, preferentially from 10/90 to 90/10, preferentially from 15/95 to 95/15, preferentially from 20/80 to 80/20, preferentially from 25/75 to 75/25, preferentially from 30/70 to 70/30. This ratio is, for example, equal to 30/70 or equal to 70/30. This ratio most preferentially ranges from 35/65 to 65/35, preferentially from 40/60 to 60/40, preferentially from 45/55 to 55/45. It is, for example, equal to 50/50.

In the present invention, the term "protein" is in the broad sense, such as it is usually understood by those skilled in the art. This covers in particular the proteins regardless of the method of obtaining them, and regardless of their number of subunits. This also covers the protein fragments, the peptides and the oligopeptides. They may be native proteins, recombinant proteins or fusion proteins. They are preferentially proteins comprising at least 5 amino acids, preferentially at least 10 amino acids, preferentially at least 50 amino acids, most preferentially at least 100 amino acids. It is understood that the protein that is of use in the invention, when it is naturally derived, for example from a plant, is generally an isolated protein.

In the present invention, the proteins are preferentially chosen from therapeutic proteins or proteins intended for industrial use. These therapeutic proteins can be chosen, in a nonlimiting manner, from enzymes, cytokines, hormones, growth factors, plasma factors, vaccines and antibodies. Examples of such therapeutic proteins are erythropoietin, insulin, monoclonal antibodies and growth hormones.

The proteins intended for industrial use are preferentially enzymes, preferentially β-amylases.

A first subject of the invention relates to the use of a combination of a polyol (i) consisting of 12 carbon atoms and of a polyol (ii) consisting of 4 to 6 carbon atoms, in particular as defined above, as protein stabilizer.

For the purposes of the present invention, the term "protein stabilizer" is intended to mean an agent which is in particular capable of preventing or slowing down the loss of activity of a protein. This loss of activity can in particular occur when the protein is subjected to stresses, for example physical and/or chemical and/or mechanical stresses, for example to variations in temperature, pH or humidity.

Preferentially, the stabilizing agent is used to stabilize proteins subjected to cryogenization and/or lyophilization treatments and/or storage, in particular storage in solution, and/or heat treatment, in particular by heating, in particular by heating in solution.

This capacity to stabilize proteins can be determined by those skilled in the art by measuring the activity of the proteins subjected to one or more stresses, in the presence or absence (control) of the test agent. This activity can for example be enzymatic and/or pharmacological and/or antigenic in nature. To measure this activity, any usual technique known to those skilled in the art can be used, depending on the protein in question. It is for example possible to carry out the measurement according to the method described in example 1 below.

The present invention also relates to a protein composition comprising a protein, a polyol (i) consisting of 12 carbon atoms and a polyol (ii) consisting of 4 to 6 carbon atoms.

Preferentially, the polyols (i) and (ii) are as defined above, preferentially in a dry weight ratio as defined above.

Generally, in this protein composition, the proteins represent from 0.01% to 80.0% of the dry matter, preferentially from 1.0% to 40.0%, for example from 1.0% to 10.0%, or from 10.0% to 30.0%, these percentages being expressed by dry weight of proteins relative to the total weight of dry matter of said composition.

Preferentially, in this protein composition, the ratio of the amount of proteins to the combination in accordance with the invention ranges from 0.5/99.5 to 99.5/0.5, preferentially from 0.5/99.5 to 50.0/50.0, more preferentially from 0.5/99.5 to 10.0/90.0, for example from 1.0/99.0 to 5.0/95.0, these ratios being expressed by dry weight of proteins relative to the dry weight of the combination in accordance with the invention.

The protein composition in accordance with the invention can be in the form of a pulverulent composition or of a liquid composition.

When the protein composition is in liquid form, it generally comprises from 0.02% to 50.00% of proteins, these percentages being expressed by dry weight of proteins relative to the total weight of said liquid protein composition.

Preferentially, the protein composition in accordance with the invention is a therapeutic protein composition.

The term "therapeutic protein composition" is intended to mean a therapeutic composition using proteins as active ingredient. These may be proteins of the same nature or a mixture of therapeutic proteins.

Preferentially, the therapeutic protein composition in accordance with the invention is in liquid form, preferentially in the form of an injectable solution, or in the form of a pulverulent composition for injectable solution.

Those skilled in the art understand the term "pulverulent composition for injectable solution" to mean typically a lyophilized pulverulent composition, intended to be reconstituted extemporaneously using the appropriate solvent.

Those skilled in the art know how to formulate these injectable solutions, in particular in such a way that they meet the regulatory requirements on the subject.

When the therapeutic protein composition is in liquid form, in particular in the form of an injectable solution, it generally comprises from 0.01% to 50.00% of therapeutic proteins, preferentially from 0.02% to 30.00%, more preferentially from 0.02% to 25.00%, for example from 0.03% to 5.00%, these percentages being expressed by dry weight of therapeutic proteins relative to the total weight of said liquid therapeutic protein composition.

In another embodiment of the invention, the protein composition is a protein composition intended for industrial use.

The term "protein composition for industrial use" is intended to mean a composition comprising a protein that is of use in an industrial process. This protein composition, in the present invention, is preferentially an enzymatic composition, preferentially a β-amylase composition, in particular a composition of β-amylase from wheat (more commonly referred to as "WBA" for "Wheat Beta-Amylase").

When this protein composition, in particular β-amylase composition, is in liquid form, in particular in the form of an aqueous solution, it generally comprises from 0.1% to 50.0% of proteins, preferentially from 5.0% to 25.0%, preferentially from 10.0% to 25.0%, these percentages being expressed by dry weight of proteins relative to the total weight of the liquid composition.

The protein compositions in accordance with the invention can also comprise any other compound well known to those skilled in the art for the application in question.

For example, the therapeutic protein compositions of the invention can include non-protein active ingredients and/or additives.

Examples of additives, in particular that are of use in the field of injectable solutions, are:
  osmotic agents, typically including glucose and NaCl;
  pH regulators, for example buffer systems of the lactate or gluconate type;
  protein stabilizers other than the combination in accordance with the invention, for example amino acids such as lysine and arginine, carrier proteins, hydrocolloids, surfactants, or native or modified cyclodextrins.

Because it is not necessary for obtaining the protein-stabilizing effect sought in the present invention, the protein compositions in accordance with the invention generally comprise less than 50.0% of protein stabilizers other than the combination in accordance with the invention, in particular of carrier proteins, of trehalose, or of polysaccharides, preferentially less than 20.0%, more preferentially less than 5.0%, most preferentially less than 0.1%, this percentage being expressed by dry weight of protein stabilizers other than the combination in accordance with the invention, relative to the total weight of dry matter of the protein compositions. In particular, the protein compositions in accordance with the invention can be free of protein stabilizers other than the combination in accordance with the invention.

A subject of the present invention is also a process for preparing a protein composition in accordance with the invention, comprising mixing together a protein, a polyol (i) consisting of 12 carbon atoms and a polyol (ii) consisting of 4 to 6 carbon atoms.

Preferentially, the polyols (i) and (ii) are as defined above, preferentially in a dry weight ratio as defined above.

Finally, a subject of the present invention is a process for stabilizing proteins, characterized in that it consists in adding, to proteins, a combination of a polyol (i) consisting of 12 carbon atoms and a polyol (ii) consisting of 4 to 6 carbon atoms.

Preferentially, the proteins and polyols (i) and (ii) are as defined above, preferentially in a dry weight ratio as defined above.

The examples which follow make it possible to understand the invention more clearly, without however limiting the scope thereof.

EXAMPLE

In this example, the capacity of various carbohydrates to stabilize proteins was tested on an enzymatic protein, a wheat β-amylase (WBA). The level of denaturation of the protein was evaluated by measuring the loss of enzymatic activity of the WBA.

Aqueous solutions comprising 0.4% of WBA and 20% of carbohydrate were prepared, these percentages being expressed by dry weight relative to the total weight of the aqueous solution.

These solutions were then subjected to a heat treatment at 70° C. for 3 minutes. This treatment makes it possible in particular to accelerate the denaturation which normally occurs during storage in solution over a longer period of time, and thus makes it possible to mimic the effects of such a storage.

After heat treatment, this solution was incubated in the presence of starch, which is a WBA substrate. The reaction was stopped by adding sodium hydroxide. The enzymatic activity was measured by means of a back titration assay with sodium thiosulfate. A percentage loss of activity was calculated from the activity measurements obtained before heat treatment for each assay.

The results obtained are given in Table 1.

In order to facilitate reading, the 1st column indicates whether the assays are intended to illustrate the invention ("IN-X"), whether they are comparative assays ("CP-X"), or whether they are assays illustrating the prior art ("AA-X").

Columns 2 to 4 give indications regarding the carbohydrates (i) and (ii) used. The 4th column indicates the dry weight ratio of the carbohydrate (i) to the carbohydrate (ii) used in the assays.

The 3rd column indicates the loss of activity measured according to the method described above. The 4th column indicates whether there is synergy between the carbohydrates (i) and (ii) used in each assay. This synergy effect was calculated on the basis of the values of loss of activity obtained when the carbohydrates were used alone, at 20%. These values, weighted by the proportions of carbohydrates of the combination in question, made it possible to determine the values expected for a simple additive effect. The values of loss of activity actually obtained for the combination in question were subtracted from the values thus calculated. Thus, a positive result denotes a synergy, whereas a result equal to 0 indicates an absence of synergy, and a negative results indicates an antagonism. The annotation "+" was used to denote the combinations for which a result greater than +4% was obtained; the annotation "++" denotes a result greater than +6%; the annotation "+++" denotes a result greater than +10%; the annotation "0" denotes a result of 0% (absence of synergy); the annotation "−" denotes a negative result (antagonism).

The assays IN-1 to IN-5 show that there is synergy between the carbohydrates (i) and (ii) when a combination of polyols in accordance with the invention is used. No synergy was on the other hand observed in the comparative assays and the assays illustrating the prior art. For the assays CP-1, CP-2 and CP-4, on the other hand, an antagonism occurs between the carbohydrates (i) and (ii).

Furthermore, likewise in absolute values, the combinations in accordance with the invention are those which show the best results: a lower loss of activity was observed using the combinations in accordance with the invention.

TABLE 1

| | Carbohydrates used | | | Effect | |
|---|---|---|---|---|---|
| | Carbohydrate (i) | Carbohydrate (ii) | Ratio (i)/(ii) | Loss of activity | Synergy |
| IN-1 | MALTITOL C12 polyol | SORBITOL C6 polyol | 50/50 | 17% | +++ |
| IN-2 | MALTITOL C12 polyol | MANNITOL C6 polyol | 50/50 | 21% | ++ |
| IN-3 | MALTITOL C12 polyol | XYLITOL C5 polyol | 70/30 | 20% | + |
| IN-4 | MALTITOL C12 polyol | XYLITOL C5 polyol | 50/50 | 23% | +++ |
| IN-5 | MALTITOL C12 polyol | 50% MANNITOL 50% SORBITOL C6 polyol | 40/60 | 22% | +++ |
| CP-1 | SORBITOL C6 polyol | XYLITOL C5 polyol | 50/50 | 53% | − |
| CP-2 | SORBITOL C6 polyol | MANNITOL C6 polyol | 50/50 | 51% | − |
| CP-3 | MANNITOL C6 polyol | XYLITOL C5 polyol | 50/50 | 49% | 0 |
| CP-4 | TREHALOSE C12 sugar | MANNITOL C6 polyol | 50/50 | 49% | − |
| AA-1 | MALTITOL C12 polyol | TREHALOSE C12 sugar | 50/50 | 26% | 0 |
| AA-2 | TREHALOSE C12 sugar | — | 100 | 36.6% | Not relevant |

The invention claimed is:

1. A process of stabilizing proteins, comprising adding to a protein to be stabilized a combination of a polyol (i) consisting of 12 carbon atoms and of a polyol (ii) consisting of 4 to 6 carbon atoms,
   wherein said protein to be stabilized is a therapeutic protein selected from the group consisting of enzymes, cytokines, hormones, growth factors, plasma factors, vaccines, and antibodies, or is an enzyme intended for industrial use, and
   subjecting said protein to be stabilized to at least one of cryogenization, lyophilization treatments, and storage,
   wherein the polyol (i) is maltitol, and
   wherein a dry weight ratio of said polyol (i) to said polyol (ii) ranges from 50/50 to 75/25.

2. The process according to claim 1, wherein said polyol (ii) comprises at least one of sorbitol, xylitol, and mannitol.

3. A process for preparing a protein composition comprising mixing together a protein, a polyol (i) consisting of 12 carbon atoms, and of a polyol (ii) consisting of 4 to 6 carbon atoms,
   wherein said protein is a therapeutic protein selected from the group consisting of enzymes, cytokines, hormones, growth factors, plasma factors, vaccines, and antibodies, or is an enzyme intended for industrial use, and
   subjecting said protein composition to at least one of cryogenization, lyophilization treatments, and storage,
   wherein the polyol (i) is maltitol, and
   wherein a dry weight ratio of said polyol (i) to said polyol (ii) ranges from 50/50 to 75/25.

4. The process according to claim 1, wherein said protein to be stabilized is selected from the group consisting of erythropoietin, insulin, monoclonal antibodies, and growth hormones.

5. The process according to claim 1, wherein said protein to be stabilized is a β-amylase.

* * * * *